US008163558B2

(12) United States Patent
Parada Valdecantos et al.

(10) Patent No.: US 8,163,558 B2
(45) Date of Patent: Apr. 24, 2012

(54) **PLASMIDS FOR TRANSFORMING BACTERIA OF THE *ACIDITHIOBACILLUS* SPP. GENUS, AND TRANSFORMATION METHOD**

(75) Inventors: Pilar A. Parada Valdecantos, Nuñoa (CL); Patricio Ernesto Martinez Bellange, Ñuñoa (CL)

(73) Assignee: Biosigma S.A., Colina (CL)

( * ) Notice: Subject to any disclaimer, the term of this patent is extended or adjusted under 35 U.S.C. 154(b) by 403 days.

(21) Appl. No.: 12/174,374

(22) Filed: Jul. 16, 2008

(65) Prior Publication Data

US 2009/0035864 A1 Feb. 5, 2009

(30) Foreign Application Priority Data

Jul. 19, 2007 (CL) .................................. 2115-2007

(51) Int. Cl.
*C12N 15/74* (2006.01)
(52) U.S. Cl. ..................... 435/476; 435/320.1; 536/24.1
(58) Field of Classification Search ........................ None
See application file for complete search history.

(56) References Cited

U.S. PATENT DOCUMENTS

| | | | |
|---|---|---|---|
| 5,348,888 A * | 9/1994 | Shiratori et al. ........... | 435/320.1 |
| 7,601,530 B2 | 10/2009 | Sugio et al. | |
| 7,691,383 B2 * | 4/2010 | Chakrabarty et al. ...... | 424/185.1 |
| 7,700,343 B2 * | 4/2010 | Ohata et al. ................ | 435/252.1 |
| 2006/0031963 A1 * | 2/2006 | Schopfer et al. ............. | 800/282 |
| 2006/0094094 A1 * | 5/2006 | Sugio et al. .................. | 435/168 |

FOREIGN PATENT DOCUMENTS

CL 131-2006 5/2006

OTHER PUBLICATIONS

Liu et al. "Construction and Characterization of a *recA* Mutant of *Thiobacillus ferrooxidans* by Marker Exchange Mutagenesis." *Journal of Bacteriology*. vol. 182. No. 8. 2000. pp. 2269-2276.

Liu et al. "Genetic transfer of InP, IncQ, IncW plasmids to four *Thiobacillus ferrooxidans* strains by conjugation." *Amils A. Ballester (Ed) International Biohydrometallurgy Symposium*. 1999. pp. 39-49.

Peng et al. "Solid Medium for the Genetic Manipulation of *Thiobacillus ferrooxidans*." *J. Gen. Appl. Microbil*. vol. 40. 1994. pp. 243-253.

Yankofsky et al. "Genetic Transformation of Obligately Chemolithotrophic Thiobacilli." *J. of Bacterbiology*. vol. 153. No. 2. 1983. p. 652-657.

English et al. "Use of Electroporation to Generate a *Thiobacillus neapolitanus* Carboxysome Mutant." *Applied and Environmental Microbiology*. 1995. pp. 3256-3260.

Rawlings. "The evolution of pTF-FC2 and pTC-F14, two related plasmids of the IncQ-family." *Plasmid*. vol. 53. 2005. pp. 137-147.

Kusano et al. "Electrotransformation of *Thiobacillus ferrooxidans* with Palsmids Containing a *mer* Determinant." *J. of Bacteriology*. vol. 174. No. 20. 1992. pp. 6617-6623.

(Continued)

*Primary Examiner* — Albert Navarro
*Assistant Examiner* — Ginny Portner
(74) *Attorney, Agent, or Firm* — Merchant & Gould P.C.

(57) ABSTRACT

The present invention discloses functional plasmids in bacteria of the *Acidithiobacillus* genus, such as the *Acidithiobacillus ferrooxidans*, *Acidithiobacillus thiooxidans* and *Acidithiobacillus caldus* species. And a method to successfully transform bacteria of the *Acidithiobacillus* genus, such as the *Acidithiobacillus ferrooxidans*, *Acidithiobacillus thiooxidans* and *Acidithiobacillus caldus* species, with these plasmids.

13 Claims, 5 Drawing Sheets

OTHER PUBLICATIONS

Applicant's Response Brief to Opposition Brief filed Aug. 7, 2008 in Chilean Application No. 2115-07, p. 1-15.

d'Hugues P.; Foucher S.; Galle-Cavalloni P.; Morin D., "Continuous bioleaching, of chalcopyrite using a novel extremely thermophilic mixed culture", Int. J. Miner. Process., 2002, p. 1-13.

English translation of CL 131-2006 (Biosigma S.A.), Feb. 1, 2006, p. 1-12.

Groudev, S., "Leaching of Cooper-Bearing Mineral Substrates with Wild Microflora and with Laboratory-Bred Strains of *Thiobacillus ferroxidans*", Deparment of Mineral Processing Higher Institute of Mining and Geology Sofia 1156, Bulgaria, p. 485-503.

JM Modak et al., Hidrometallurgy 42 (1996), p. 51-61.

Opposition Brief filed Feb. 12, 2008 in Chilean Application No. 2115-07, pp. 1-5.

Pretorius, I.M. et al, "Nucleotide sequence of the gene encoding the nitrogenase iron protein of *Thiobacillus ferrooxidans*." J. Bacteriol. Jan. 1987; 169 (1): 367-70.

Rawlings, D.E. "Relevance of Cell Physiology and Genetic Adaptability of Biominig Microorganisms to Industrial Processes" Ed. by Rawlings, D.E. and Barrier, D.J., Springer-Verlag Berlin Heidelberg 2007, p. 177-198.

Rawlings, D.E. and Woods, D.R., "Development of improved biomining bacteria" Ed. by Gaylarde, C.G. and Videla, H.A., Cambridge, Eng.; New York: Cambridge University Press, 1995, p. 63-84.

Scheiner et al., "Biotechnology in Minerals and Metal Processing", Littleton, Colorado, USA (1989), p. 141-149.

Van Zyl,L.J., et al., *Acidithiobacillus caldus* plasmid pTC-F14 replicon, complete sequence. Accession in NCBI:AF325537 (Oct. 3, 2003) 1 page.

\* cited by examiner

Figure 1

```
ACC ATG ATT ACG CCA AGC GCG CAA TTA ACC CTC ACT AAA GGG AAC AAA AGC TGG GTA CCG GGC CCC
                                        Promotor nit
CCC TCG AGT TTT GCG CAA ATT TAA ACG ACC TGC CTG TCT TGC CAA TCC ATC CCG CCC ACT TCC TTG
                                                                    HindIII            EcoRI
ACA ATA CCA ACC GGT CGG TCT TAG ATG GGG GCC ACA CTG AAA ATT TGA AAG CTT GAT ATC GAA TTC
            Thr Gly Arg Ser Stp Met Gly Ala Thr Leu Lys Ile Stp Lys Leu Asp Ile Glu Phe
                BamHI        XbaI        NotI                   SacI
CTG CAG CCC GGG GGA TCC ACT AGT TCT AGA GCG GCC GCC ACC GCG GTG GAG CTC CAC CAC CAC CAC
Leu Gln Pro Gly Gly Ser Thr Ser Ser Arg Ala Ala Ala Thr Ala Val Glu Leu His His His His
            SacI
CAC CAC TGAgagctCCAATTCGCCCTATAGTGAGTCGTATTACGCGCGCTCACTGGCCGTCGTTTTACAACGTCGTGACTGGGAAA
His His Stp
```

PLASMIDS FOR TRANSFORMING BACTERIA OF THE *ACIDITHIOBACILLUS* SPP. GENUS, AND TRANSFORMATION METHOD

SCOPE OF THE INVENTION

The present invention discloses functional plasmids in bacteria of the *Acidithiobacillus* genus, such as the *Acidithiobacillus ferrooxidans*, *Acidithiobacillus thiooxidans* and *Acidithiobacillus caldus* species. And a method for successfully transforming bacteria of the *Acidithiobacillus* genus, such as the *Acidithiobacillus ferrooxidans* and *Acidithiobacillus thiooxidans* and *Acithiobacillus caldus* species, with these plasmids.

BACKGROUND OF THE INVENTION

Bacteria of the *Acidithiobacillus* genus are acidophilic, autotrophous and chemolithotrophs, in other words, they live with acid pHs of 0 to 4, their source of carbon is $CO_2$, and their source of energy is inorganic compounds. Two of the species of this genus are of vital importance in biomining: *Acidithiobacillus ferrooxidans*, and *Acidithiobacillus thiooxidans* On the other hand, *Acidithiobacillus caldus* is becoming increasingly important in biomining processes.

Biomining is, generally speaking, the use of microorganisms for extracting metals from ores. Its most traditional and important expression is bioleaching, but biomining is more than this process alone, it is also the monitoring and intervention of the microorganisms involved—insofar as these techniques are complex and constantly developing—as well as laboratory-level research associated with the improvement of processes or the development of new technologies.

Bioleaching is defined as method for solubilizing metals from complex matrixes in an acid medium, employing the direct or indirect action of microorganisms (Rawlings D. E. Microb. Cell Fact. 2005; 4(1):13). It is direct when the microorganisms act on the metal or on its counter ion, releasing an ion of the metal of interest into the solution in both cases. On the other hand, it is indirect when the microorganism does not have either the metal of interest or its counter ion as a substrate, but generates chemical conditions that accelerate and favour solubilization of the said metal, whether by acidification of the medium, (for example, generating sulphuric acid) or because it generates an oxidizing agent that finally interacts with the salt (metal and counter ion) that needs to be solubilized. Species belonging to the *Acidithiobacillus* genus, both *Acidithiobacillus ferrooxidans* and *Acidithiobacillus thiooxidans*, and *Acidithiobacillus caldus*, are capable of producing elements that increase the oxidizing velocity of reduced sulfur compounds (such as sulfide, elemental sulfur, thionates, etc.) using oxygen as an electronic acceptor. During this process, they generate sulfuric acid as an end product, and reducing-species such as sulfite and thiosulfate, as intermediate products, which makes solubilizing the metals associated to sulfides in the ore possible particularly speaking, *Acidithiobacillus ferrooxidans* contributes with biological components that favor the oxidization of iron (II) to iron (III) using oxygen as an electron acceptor. The generated iron (III) is a great oxidizing agent that can oxidize the sulfides present, or any compound that needs to be oxidized.

Given the importance of bacteria of the *Acidithiobacillus* genus, it would be convenient to be able to genetically manipulate them—having an effective method for transforming them—whether for improving their oxidizing activity, incorporating functions of interest such as resistance to toxic compounds into them, or for getting to know more about their metabolism.

The most traditional way to modify the genetic load of bacteria is using the transformation process. This process consists in directly integrating a DNA fragment of interest into a microorganism to be transformed. There are a variety of transformation techniques in the technique, one of the most usual of which is electroporation.

All manipulations of *Acidithiobacillus* spp. are complex; even culturing it in the laboratory is not simple. This is because it must be kept at an extremely acid pH, and the ores it employs as a substrate are problematic, or precipitate in the medium in the form of salts, as occurs with iron, or are particulates such as elemental sulfur. The presence of iron precipitate can be observed with the naked eye as a reddish nucleus in colonies. On the other hand, bacteria adhere to particulate material, leading to a loss of biomass in the wash stages that are necessary for any microbiological manipulation technique.

Because of the above, it is necessary to be provided with an adequate transformation method especially designed for these bacteria. A method has been designed with the purpose of successfully transforming bacteria of the *Acidithiobacillus* genus such as the *Acidithiobacillus ferrooxidans*, *Acidithiobacillus thiooxidans* and *Acidithiobacillus caldus* species.

One of the most usual techniques used for the transformation of microorganisms, as stated above, is electroporation. Electroporation basically consists in temporarily permeabilizing the cell membrane, employing brief high-intensity electrical discharges. Transient permeable regions or structures known as micropores, through which the vectors enter the cells, are generated in the membrane.

Electroporation of *Acidithiobacillus* spp. becomes difficult if ferric sulfide has been used as a substrate, because the presence of ferrous ion salts associated to the bacteria could harm the transformation vectors. On the other hand, if sulfur has been used as a substrate, the cultures will be depleted after washings because part of the bacteria will be lost adhered to the particulate material.

But not only the method should be differentiated, the genetic vectors employed should have certain characteristics that allow them to be functional inside the cell. One of these corresponds to the origins of replication (ori). In some cases they are specific for different genera and even specific for one particular species, and because of this, even if we were able to transform an *Acidithiobacillus* spp., we would not achieve expression of the vector unless we had a replication system that were appropriate for *Acidithiobacillus* spp. This ideally requires that an *Acidithiobacillus* spp. plasmid be obtained, and its ori identified to incorporate it into the transformation vector. It is also convenient to have a promoter with a strong expression to ensure transcription of the gene of interest.

Very few *Acidithiobacillus* spp. plasmids have been described to date, and much less characterized. Rawlings has studied two of them (Rawlings D. E., 2005, Plasmid 53: 137-147), but has not described their use in transformations.

In the publication by English (English et al 1995, Appl. Environ. Microbiol., 61: 3256-3260), *Acidithiobacillus neapolitanus* is transformed by electroporation with a vector constructed with the replicon of an isolated *Acidithiobacillus intermedius* plasmid and with the gene of a peptide from the formation of carboxysomes in *Acidithiobacillus neapolitanus*. In this case, even if transformation did occur, the expression of the incorporated protein was not perceived, so it cannot be given the category of a successful transformation.

Another publication dealing with the subject of *Acidithiobacillus* transformation is one by Kusano (Kusano et al, 1992, J. Bacteriol., 174: 6617-6623), in which *Acidithiobacillus ferrooxidans* are transformed but plasmids of this species are not disclosed. In fact, the authors generated vectors with a mercury-resistant operon, a mer operon, previously isolated from *Acidithiobacillus ferrooxidans*. Thirty independent strains of *Acidithiobacillus ferrooxidans* were electroporated, and the transformation only came about in one of them, with an efficiency of 120 to 200 mercury-resistant colonies per µg of vector. This transformation efficiency is very low, so it is not considered to be an adequate transformation alternative. In fact, there are no other works by Kusano dealing with this technique, and its subsequent applicability has not been verified, because it has not been possible for other groups working with *Acidithiobacillus* spp. to reproduce the results of this publication.

There are three publications in which transformation of *Acidithiobacillus* spp. by conjugation using *E. coli* as a donator is achieved (Yankofsky et al, 1983, J. Bacteriol., 153: 652-657), (Jin et al 1992, Appl. Environ. Microbiol., 58: 429-430) and (Liu et al 2000, J. Bacteriol., 182: 2269-2276), but good transformation efficiency is not obtained in any of them.

Summing up, in the state of the art there are neither specific functional plasmids for the *Acidithiobacillus* spp. genus nor a method permitting their efficient transformation, particularly that of *Acidithiobacillus ferrooxidans*, *Acidithiobacillus thiooxidans* and *Acidithiobacillus caldus* species.

This technical issue has been resolved by constructing specific functional plasmids for the *Acidithiobacillus* spp. genus, containing the origins of replication (ori) of isolated *Acidithiobacillus ferrooxidans* (Wenelen DSM 16786) and *Acidithiobacillus thiooxidans* (Licanantay DSM 17318) plasmids associated to an expression promoter isolated from the Wenelen (DSM 16786) strain, and by promoting and developing a specific transformation method for *Acidithiobacillus* spp.

Invention Abstract

The present invention discloses plasmids that allow *Acidithiobacillus* spp. bacteria such as the *Acidithiobacillus ferrooxidans*, *Acidithiobacillus thiooxidans* and *Acidithiobacillus caldus* species, to be successfully transformed, and a transformation method.

These plasmids include isolated origins of replication (ori) of plasmids obtained from *Acidithiobacillus ferrooxidans*, represented by Sequence No 1 or by its reverse complementary sequence, and from *Acidithiobacillus thiooxidans*, represented by Sequence No 2 or by its reverse complementary Sequence. And Pnit, the expression promoter of reductase, isolated from the Wenelen (DSM 16786) strain, the property of Biosigma, represented by Sequence No 3. The advantage of the Pnit promoter, as will be described later, (FIG. 3), is that it strongly stimulates the expression of the gene it regulates.

Shuttle-type cloning genetic-vectors (plasmids) which include at least one of the ori represented in Sequence No 1 and Sequence No 2, expression promoter Pnit, Sequence No 3, a second origin of replication specific for another gene, a multiple cloning site, and at least one marker or reporter gene, are described.

The transformation method includes gradually modifying the conditions under which *Acidithiobacillus* spp. are cultured, in order to make them appropriate for being transformed with the plasmids of the invention.

*Acidithiobacillus* spp. cultures adapt to a pH of 5 to 7, and the substrate is modified into a tetrathionate salt. If necessary, the substrate is first modified from iron sulfide to elemental sulfur as an intermediate substrate, and finally into the tetrathionate salt. Once the culture is stable in these conditions, it is transformed by any known transformation technique, especially by electroporation.

BRIEF DESCRIPTION OF THE DRAWINGS

FIG. 3. Shows a photograph of a gel in which the expression of a protein cloned in vectors of the invention is evaluated. pBM-3 PnH® vectors were built incorporating the rusticyanin gene of *Acidithiobacillus ferrooxidans* of our Wenelen (DSM16786) strain as a cloned gene. This vector was used to transform an *E. coli* DH5 α culture, and the cloned protein was subsequently purified using an affinity column for histidines (NTA-agarose). As a negative control, an *E. coli* DH5 α culture was transformed with a pBM-3 PnH® (vector without the cloned gene. The product of the purification was detected in a chemoluminescent western-blot, using specific antibodies recognizing the 6-histidine sequence, and developed by chemoluminescence and radio-autography. Lanes 1 and 2 correspond to purificates of two *E. coli* DH5α clones transformed with the construction that includes the *Acidithiobacillus ferrooxidans* rusticyanin gene. Lane 3 shows the negative control of the *E coli* clone transformed solely with the pBM-3 PnH® vector.

Conclusion: strong expression of the cloned rusticyanin protein is observed in the pBM-3 PnH® vector. This proves that the Pnit promoter is a promoter that strongly stimulates the expression of the gene it regulates.

Conclusion: development of transformed colonies is observed on both plates, indicating the success of the invention's transformation method. Colonies that only grew on plate A, are unstable transformants. A total of 4 stable transformants was obtained.

Conclusion: transformation of *Acidithiobacillus ferrooxidans* is stable, because the vector can be recovered.

FIG. 6.A. Shows a photograph of a gel with the result of the amplification by PCR, of the kan gene. In the lane 1 sample, the PCR substrate was an extraction of DNA from an *Acidithiobacillus ferrooxidans* strain transformed with pBM-3 PnH®. Lane 3 is the positive control, in which the PCR substrate was the purified pBM-3 PnH® plasmid, lanes 2, 4 and 5 correspond to negative controls, of which water was the substrate in lanes 2 and 5, whereas an extraction of DNA from an untransformed *Acidithiobacillus ferrooxidans* strain was used in lane 4. Lanes 6 and 7 correspond to molecular standards 100 pb and λ HindIII respectively.

Conclusion: It is observed that the transformed strain (1) presents the same band as the positive control (3) and no band is observed in the negative control of the untransformed strain (4). So the recovered plasmid corresponds to plasmid pBM-3 PnH®.

FIG. 6. B. Shows the photograph of a culture plate, corresponding to an *E. coli* transformant selection plate. An *E. coli* culture was transformed with the pBM-3 PnH® plasmid recovered from a transformed *Acidithiobacillus ferrooxidans* clone which includes a kanamycin-resistant gene. The plate corresponds to transformants sown in a Luria Bertani (LB) Agar medium supplemented with 50 µg/mL kanamycin.

Conclusion: the transformation of *Acidithiobacillus ferrooxidans* is successful, because the vector can be recovered intact and used in a new transformation.

DETAILED DESCRIPTION OF THE PREFERRED EMBODIMENTS

Having a method that allows *Acidithiobacillus* spp. bacteria to be transformed efficiently is of great importance in biomining, because it would allow these bacteria to be improved by incorporating into them genes that advantageously transform them, improving their efficiency in the processes in which they participate. To achieve this, it is fundamental to be supplied with plasmids containing origins of replication that are functional in this genus, as well as a method for making this transformation possible.

The first step to obtaining the plasmids is to be provided with *Acidithiobacillus* spp. ori. Plasmids were isolated from strains of the *Acidithiobacillus ferrooxidans* and *Acidithiobacillus thiooxidans* species for this purpose. Once these plasmids were obtained, they were sequenced and studied in order to establish the possible ori present in them.

In each case, the presence of a putative ori was determined, which in the case of Sequence No 1 corresponds to *Acidithiobacillus ferrooxidans*, and in the case of Sequence No 2, to *Acidithiobacillus thiooxidans*. It is evident to an expert in the art, that every DNA sequence is equivalent to its reverse complementary sequence. According to this, each time we refer to a certain sequence, in this case Sequences No 1 or No 2, we also refer to its reverse complementary sequence.

Being provided with specific ori for bacteria of the *Acidithiobacillus* genus allows us for the first time to generate a transformation vector with high probabilities of being successful, whether for cloning, when the generated vector does not include an expression promoter, or for expression, when the vector includes an expression promoter.

The plasmids of the invention preferably include an expression promoter isolated from the Wenelen (DSM 16786) strain, the property of Biosigma. The nitroreductase promoter, Pnit, was identified in the genome of this strain and selected for being a strong promoter that is highly expressed in different culture conditions. The Pnit is represented by Sequence No 3. By including Pnit in our vector, we make sure we have a strong expression of the gene of interest, regulated by this promoter.

Once the ori for *Acidithiobacillus*, Sequence No 1 and Sequence No 2, and the Pnit promoter, Sequence No 3 were available, transformation vectors that included them were designed.

Shuttle vectors which are functional in two different genera or species were particularly designed. In this case, apart from the ori for *Acidithiobacillus*, Sequences No 1 or No 2, the vectors include a second origin of replication that is specific for another genus. The vectors also include the Pnit promoter, a multiple cloning site, and at least one marker or reporter gene.

The second origin of replication is chosen from among any of the ones known in the state of the art, ori pUC, ori ColE1, ori p15A, ori NTP1, ori pBR345, ori pBR322, ori R6K, etc., the pUC ori is especially preferred.

A multiple-cloning site, associated to a reporter gene, is included in the genetic vector design, so that the insertion of a gene into the said cloning site determines the non-expression of the reporter gene. This makes it possible to establish whether the insertion of the gene of interest in the cloning site was successful. In order to do the cloning, one of the restriction enzymes that recognizes a sequence within the multiple-cloning site is chosen ensuring that this sequence is not present in the gene of interest.

The reporter gene associated with the cloning site is chosen from among known reporter genes which can be identified by changes of color in substrates, luminescence, or others, such as lacZ (β-galactosidase) genes, gfp (green phosphorescent protein), luc (luciferase), etc. This reporter gene is especially the β-galactosidase, lacZ gene.

The vector has a marker gene that allows its presence to be identified through selection, and is chosen from among the genes resistant to antibiotics. The gene that confers resistance to kanamycin (kan) is especially preferred.

The carryings-out that are preferred are the ones in which the multiple-cloning site also includes a Histidine tail, that is to say a sequence that codifies for 6 histidines which remain incorporated as the last amino acids at the carboxyl-end of the protein we want to express. The advantages of including this peptide lie, in the first place, in the existence of anti-histidine antibodies which can easily be used to evaluate the expression of any cloned protein, and in the second place, in that the histidine hexapeptide allows the chimerical protein that includes it to be purified in Nickel/Cadmium affinity columns.

Figure 1:
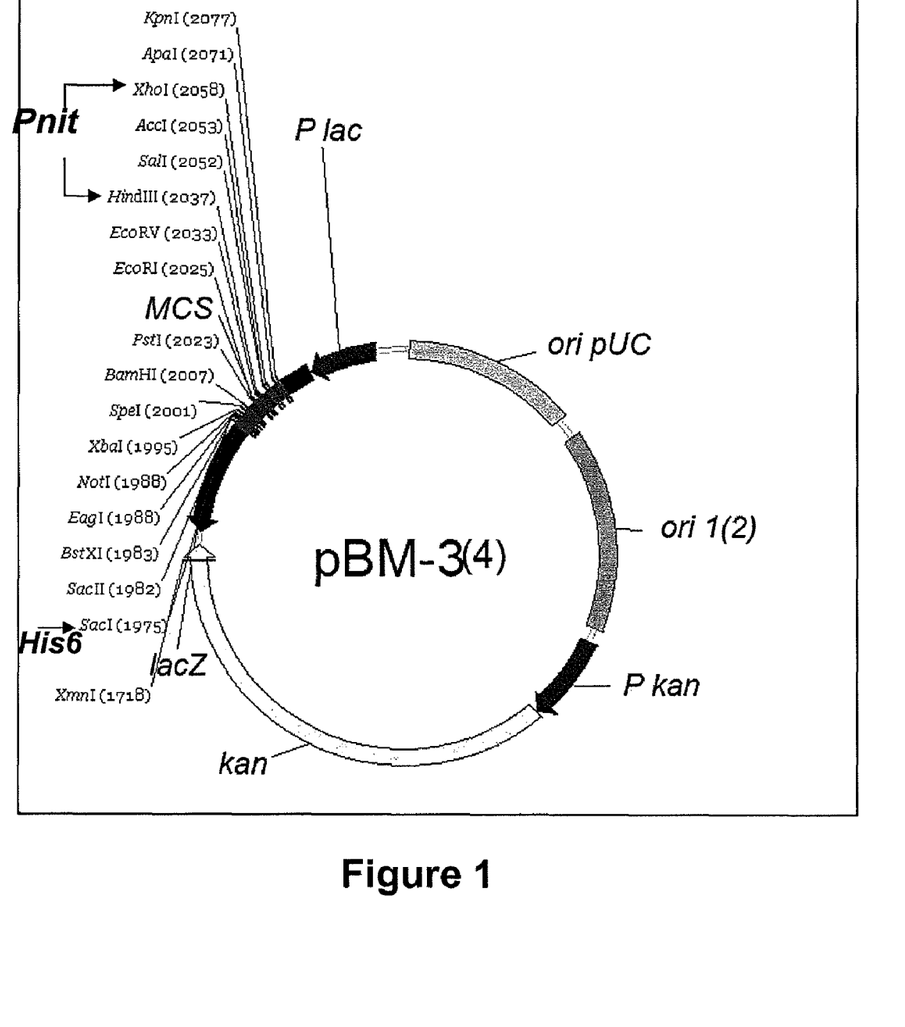
FIG. 1. Shows a diagram representing the preferred genetic vectors that are useful for transforming bacteria of the *Acidithiobacillus* genus. The diagram shows the pUC ori; ori 1 or 2 of the present invention; the gene that confers resistance to kanamycin (kan) with its respective promoter, P kan; the lacZ gene with its respective promoter, P lac, and the multiple-cloning site, MCS which includes promoter Pnit and the tail of histidines (His 6). The vector with the ori 1 of the invention corresponds to pBM-3 PnH®, and the one with the ori 2 of the invention corresponds to pBM-4 PnH®.
Figure 2:
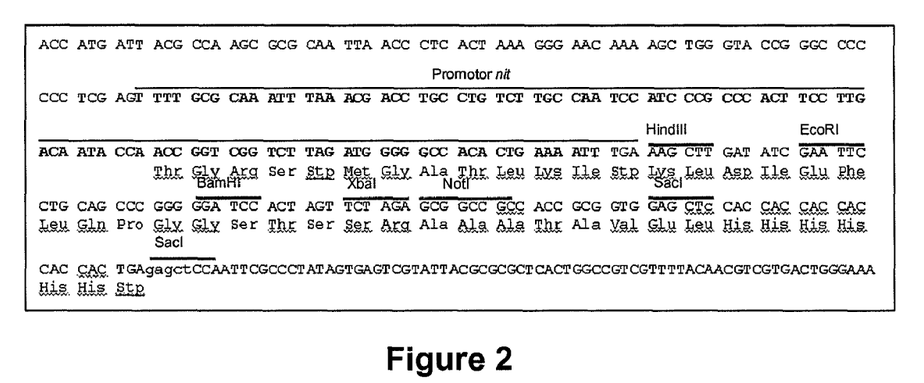
FIG. 2. Shows the sequence of the multiple-cloning site, MCS in which promoter Pnit, the cloning restriction sites, and the sequence of 6 final histidines, is shown.

FIG. 1 represents the preferred genetic vectors of the present invention, among which are the pUC ori; ori 1 or 2 of the present invention; the gene that confers resistance to kanamycin (kan) with its respective promoter, P kan; the lacZ gene with its respective promoter, P lac; and the multiple-cloning site (MCS) which includes the Pnit and the tail of histidines (His 6). The vector with ori 1 of the invention corresponds to pBM-3 PnH®, and the one with ori 2 of the invention corresponds to pBM-4 PnH®. The multiple cloning site can be observed in detail in FIG. 2.

Figure 3:
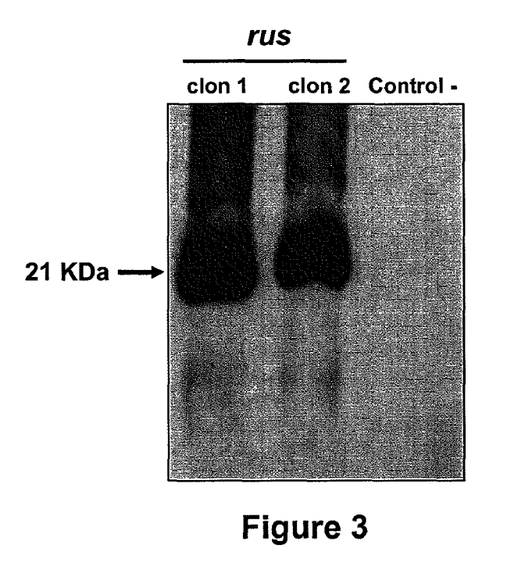

The strength of the Pnit promoter is proven in FIG. 3 which shows the expression of the rusticyanin protein of *Acidithiobacillus ferrooxidans* cloned in pBM-3 PnH®, and detected after being purified in an affinity column. The detection was carried out by means of a chemoluminescent western-blot, using specific antibodies against the Histidine sequence. Lane 1 and 2 correspond to purificates of two *E. coli* DH5α clones transformed with the construction. Lane 3, corresponds to purification of a strain transformed solely with the pBM-3 PnH® vector which is incorporated as a negative control. The strong expression obtained from the protein regulated by Pnit can be observed.

The plasmids of the invention were built with methods known in the state of the art, which essentially include the ori for Acidithiobacillus, Sequence No 1 and Sequence No 2, and the Pnit promoter, Sequence No 3.

It is evident for an expert in the art that both the ori for Acidithiobacillus, Sequence No 1 and Sequence No 2, and the Pnit promoter, Sequence No 3, can be employed independently in other genetic constructions not explicitly foreseen in this description. Each time the ori of Sequence No 1 or the ori of Sequence No 2 are incorporated into a genetic construction, expression in Acidithiobacillus spp. will improve substantially. Each time the Pnit promoter, Sequence No 3, is incorporated into a genetic construction, there will also be a strong expression of the sequence associated to the promoter. All uses of the disclosed sequences for the ends described above, will be considered to be obvious modifications of the present invention.

Once the plasmid of the invention has been constructed, it is necessary to be provided with a method that will make it possible for this plasmid to be incorporated into Acidithiobacillus spp.

The first difficulty that arises in the transformation of these bacteria lies in that the substrates they use interfere with practically all known manipulation methods. These Acidithiobacillus spp., as it is known, require a source of iron and/or sulfur as a source of energy. The A. ferrooxidans spp. species is traditionally provided with ferrous sulfate as a substrate. It is a good substrate, although when it oxidizes to ferric ion, the oxidizing power of the culture increases, interfering with the electroporation method by deteriorating the DNA vectors before transformation comes about or by increasing the possibilities of voltaic arcs—that damage the cells—forming. Another energy source that is appropriate for the Acidithiobacillus genus is elemental sulfur, which has the disadvantage of being insoluble, because of which it should be added in particulated form to the culture, and that when it is eliminated from the culture it carries away many of the bacteria present, because they adhere to the substrate particles.

In order to resolve this first problem encountered in the process, we have opted for the use of a soluble source of sulfur: tetrathionate salts. We have found that Acidithiobacillus spp. bacteria accept the tetrathionate salts as a source of sulfur if the cultures are gradually adapted.

In the first stage, commonly used ferrous sulfate should be replaced with elemental sulfur which should later in turn be replaced with tetrathionate salts. Each change of substrate is generated by taking an inoculum from the original culture and letting it grow in a different substrate medium. It is necessary to wait for the culture to be stable before carrying out a new change of medium. This will usually occur within a period of 3 days to 2 weeks, most commonly a week after the change of substrate was generated.

A second inconvenience encountered in the transformation of Acidithiobacillus spp. is the extremely acid pH in which these bacteria develop, which is usually within ranges even lower than pH 2.

A selection gene that gives the transformed cell a characteristic by which it can be easily differentiated from the untransformed cell, is normally incorporated into the transformation vector to verify whether transformation came about or not. In most cases a gene that confers resistance to some antibiotic is incorporated, and the transformants are selected by incorporating this antibiotic into the culture medium. The vast majority of antibiotics, which are complex organic molecules, are denaturalized and their activity partially or totally inhibited at an acid pH. So pH 2 makes the selection of transformed Acidithiobacillus spp. difficult.

In order to resolve this problem, the method of the invention includes gradual modification of the culture pH. Increases in the pH of the medium are carried out half to one point at a time, and each increase is carried out at 5 to 15-day intervals, ensuring culture stability at all times prior to carrying out a new pH increase.

The pH of the culture medium is increased by preparing culture medium solutions of a composition equal to the original, but adjusted to a higher pH (half to one point at a time) with Sodium Hydroxide.

The increase in the culture pH and the change of substrate of the culture can be carried out simultaneously or sequentially, and it makes no difference which comes first.

Once a stable Acidithiobacillus spp. culture at a near neutral pH of 5 to 7 and using tetrathionate salts as substrate is obtained, transformation of the culture can be carried out with any technique known in the art, especially with electroporation. If the transformation method requires it, ice-cold washing with an appropriate buffer is carried out before the transformation.

Once the transformation is completed, with the plasmids of the invention, the cells should be grown on plates containing the selection element (whose resistance is contained in the transformed vector). The plates are incubated at 25-45° C. for 7 to 14 days. The colonies that grow correspond to the successfully transformed cells.

Some examples of carryings-out of the invention are presented below. They should by no means be considered limitative but rather illustrative of the present invention.

EXAMPLES

Example 1

Construction of the Vector

A fragment containing the ori, represented in Sequence No 1 was amplified through PCR, and on completion, oriented by means of restriction enzymes (PagI/HpaI). The kan fragment was obtained from the pTOPO vector and connected in the ScaI site to the multiple cloning site (MCS) shown in FIG. 2, and to the pUC origin of replication obtained from the pBluescript vector. The resulting fragment was linked in the PagI/HpaI sites to ori 1, through the use of the T4 ligase enzyme. The Pnit promoter in the XhoI/HindIII restriction sites, and the sequence of 6 histadines in the SacI site, were subsequently added to the genetic vector.

The resulting plasmid, named pBM-3 PnH®, has an expected size of approximately 4500 bp, and its structure is presented in FIG. 1.

The product of the liaison was used for transforming E. coli by means of electroporation, under standard conditions. Transformants were selected in an LB agar medium containing 50 µg/mL of Kanamycin.

Kanamycin-resistant colonies were cultivated in an LB kan 50 µg/mL liquid medium, the plasmidial DNA of resistant clones was isolated, and identified as the plasmid designed by a map of restriction (enzymatic cuts with HindIII, HpaI, EcoRI, SmaI, etc.), and PCR amplification of different sectors present in the constructed plasmid. The results confirmed that the isolated plasmid is the constructed vector.

Example 2

Transformation by Electroporation of *Acidithiobacillus ferrooxidans*

Firstly, the culture substrate was adapted to the substrate of the invention, Tetrathionate salts, and the pH of the cultures was kept constant.

A culture of 10 mL of *Acidithiobacillus ferrooxidans* which uses ferrous sulfate as a source of sulfate, and grows at pH 2.5, was provided.

An inoculum of 1 mL of the said culture was sampled and transferred to 9 mL of a 1% S medium. The culture was incubated during 1 week at 30° C.

An inoculum of 1 mL of the culture in S was then transferred to 9 mL of 9K 0.1% Tetrathionate medium, the composition of which is shown in Table 1. The culture was incubated during 1 week at 30° C.

TABLE 1

9K Liquid Medium, 1X

| Component | Concentration, (g/L) |
|---|---|
| $(NH_4)_2SO_4$ | 3.0 |
| $K_2HPO_4$ | 0.5 |
| $MgSO_4\ 7\ {*}H_2O$ | 0.5 |
| KCl | 0.1 |
| $Ca(NO_3)_2$ | 0.01 |

The culture's pH was later adjusted to a pH close to neutral, maintaining the substrate.

To this end, 1 mL of the culture in 9K 1% Tetrathionate, pH 2.5, was sampled and inoculated into 9 mL of 9K 0.1%, pH 3.5 Tetrathionate medium. The culture was incubated for 1 week at 30° C. This action was repeated, inoculating a pH 4.5 medium first, and then a pH 5.5 medium.

To increase the biomass prior to transformation, 10 mL of 9K 0.1% Tetrathionate, pH 5.5 culture was inoculated in 90 mL of the same medium. This crop was left to grow one week until saturation was reached at 30° C.

An inoculum was taken from this saturated culture and diluted at 10% in the same medium, and incubated overnight to obtain a fresh culture.

The following morning, cells were collected by 10-minute centrifugation at 8,000 rpm. The cells were ice-cold washed with 40 mL of an A solution (9K salt base, pH 1.8). A second cold wash was subsequently carried out with 40 mL of solution B (PBS 5 mM, Sacarose 0.3 M, 10 mM EDTA, pH 8.0). Finally, a third ice-cold wash was performed with 30 mL of electroporation buffer, solution C (PIPES 3 mM®, Sacarose 272 mM, pH 6.4).

Following these washes, the pellet was resuspended in 1 mL of solution C, and kept on ice until electroporation.

A pBM-3 PnH® vector was employed in the electroporation, as illustrated in Example 1.

A volume of 10 μL with 7 g of the pBM-3 PnH® vector was employed, and its DNA then dialyzed for 30 minutes. 400 μL of cells were electroporated in 0.2 cm cuvettes at 2,500-3,000 V and 400Ω.

Each of the 400 μL electroporated cells were inoculated separately in 10 mL of 9K 0.1% Tetrathionate medium, with no selection. In addition, as a negative control, 400 μL of non-electroporated cells were independently inoculated with 10 mL of 9K 1.0% Tetrathionate medium, in a different flask. All cultures were incubated overnight, with agitation, at 30° C.

Figure 4:
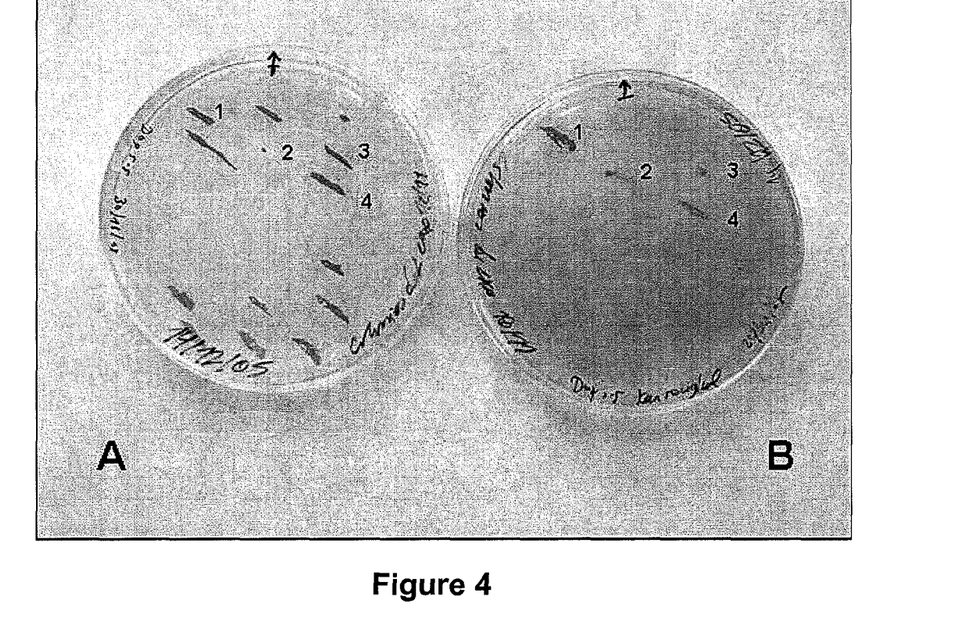
FIG. 4. Shows a photograph of two culture plates corresponding to *Acidithiobacillus ferrooxidans* transformant in selection plates. The *Acidithiobacillus ferrooxidans* culture was transformed with the pBM-3 PnH® plasmid which includes a kanamycin-resistant gene. Plate A. Corresponds to the transformants sown in a medium without kanamycin, DOP pH 5.5 initially obtained from transformation with pBM-3 PnH® by selection in DOP kan 50 µg/mL pH 5.5. Plate B. Corresponds to a replica on a plate with kanamycin, DOP kan 50 µg/mL pH 5.5.

The next day, DOP plates were prepared with 50 μg/mL Kanamycin, pH 5.5. The DOP solid medium is described in the literature (Liu, Z. et al 1999, p. 39-49, R. Amils and A. Ballester (Ed.) International Biohydrometallurgy Symposium, Elsevier, Amsterdam, The Netherlands), (Peng, J. B. et al, 1994, J. Gen. Appl. Microbiol. 40:243-253). Two hundred (200) μL of each culture were sampled and sown homogeneously, in duplicate, in the prepared plates. The plates were incubated for 7 days at 30° C. All plates revealed the existence of transformants. One of these plates was later replicated in DOP solid medium, pH 5.5, without Kanamycin (A.), and in DOP solid medium, pH 5.5, with Kanamycin 50 μg/mL, (B.). FIG. 4 shows a photograph of these two plates. In plate A., without Kanamycin, all initially transformed colonies were obtained. On the other hand, in plate B., with a medium of Kanamycin, only stable transformants that continued to express the gene were seen to grow. In this case, 4 stably transformed *Acidithiobacillus ferrooxidans* colonies were obtained.

A PCR test was performed on each of the 4 colonies that grew in the selective medium (B), 1, 2, 3 and 4 simultaneously; with splitters that recognize the kanamycin-resistant gene present in the transformed vector. The unmodified negative control was also included, and the pBM-3 PnH® vector was used as a template for positive controls. The results of amplification showed that the clones possessed the Kanamycin gene, and bands of identical size of those of the positive control were obtained.

Example 3

Recovery of a Vector from a Transformed Strain of *Acidithiobacillus Ferrooxidans*

Figure 5:
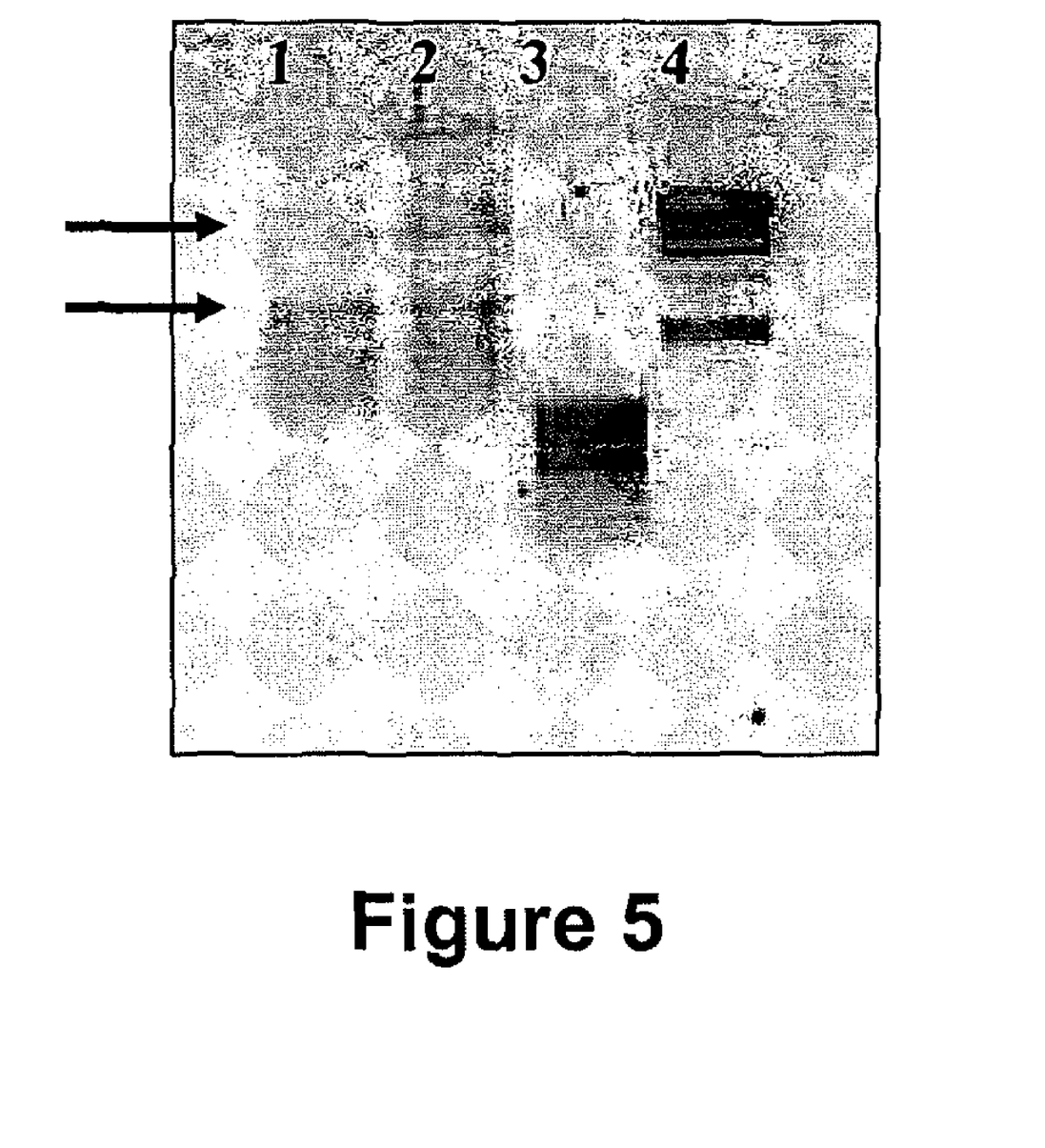
FIG. 5. Shows a photograph of a gel with the result of the extraction of plasmidial DNA from a culture of the transformed *Acidithiobacillus ferrooxidans* strain. Ten µL of the extraction mixture were loaded on the first lane, and 20 µL on the second lane, and lanes three and four correspond to molecular standards 100 pb and λ HindIII respectively.

The Plasmidial DNA was isolated by the alkaline lysis method, from a clone of *Acidithiobacillus ferrooxidans* transformed with pBM-3 PnH®, and grown in a 9K sulfur medium with a kan of 50 ug/ml. An initial gel was prepared to verify the presence of the vector, as shown in FIG. 5, where 10 μL of extract mix were placed on the first lane, and 20 μL of the same extract mix of plasmidial DNA from the transformed *Acidithiobacillus ferrooxidans* strain were placed on the second lane. The third and fourth lanes correspond to molecular standards 100 pb and λHindIII, respectively. The band displayed conforms to the expected size of the vector. This shows that, given that the vector can be recovered, transformation is stable.

Figure 6:
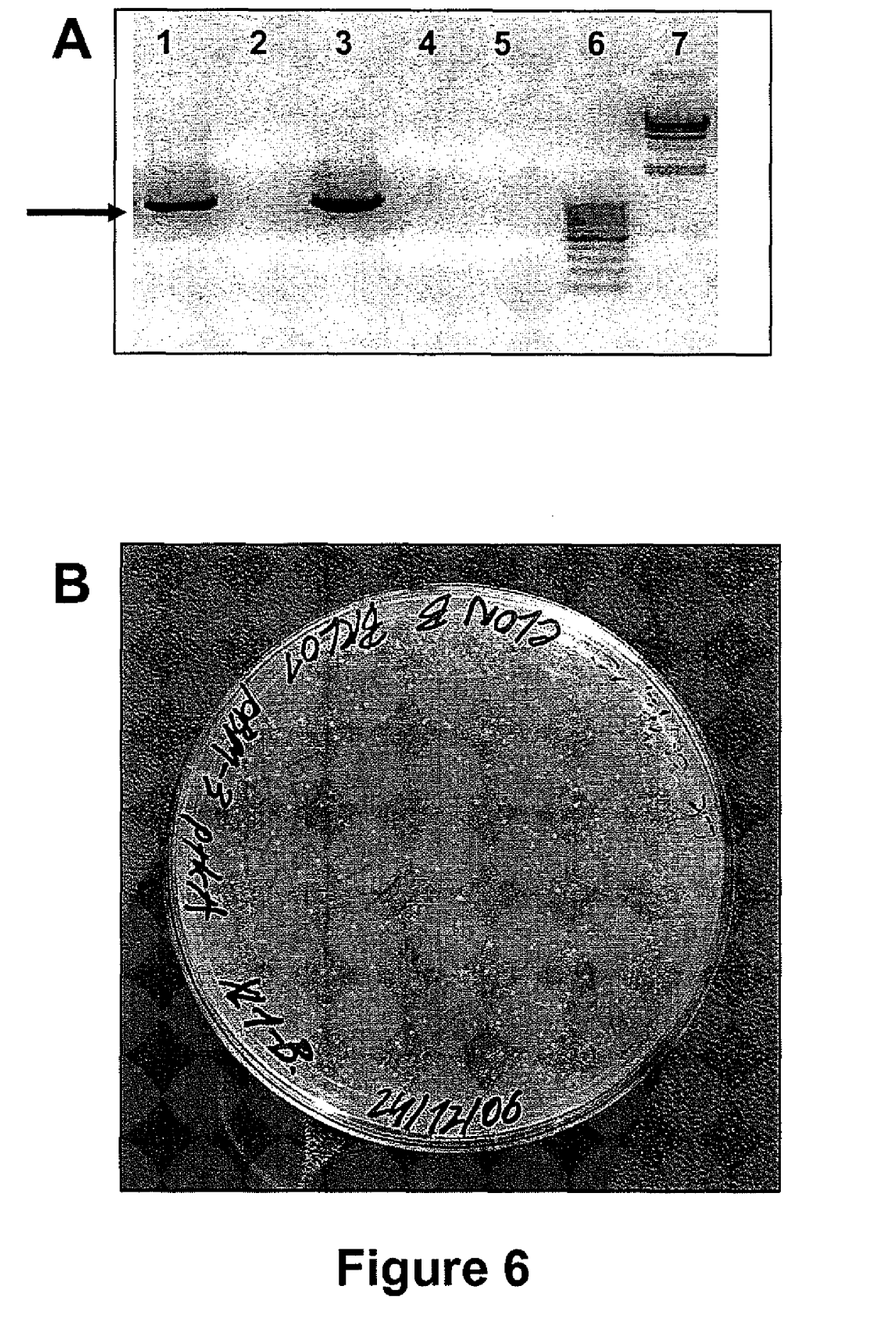

A second method of verification of the success of the transformation, a PCR amplification, was carried out on the Kanamycin (kan)-resistant gene included in the vector. PCR reactions were performed on a strain of *Acidithiobacillus ferrooxidans* transformed with pBM-3 PnH®, on an untransformed strain, on the pBM-3 PnH® vector, and on water, as a negative control. FIG. 6.A shows the result of the reactions, where lane 1 corresponds to the *Acidithiobacillus ferrooxidans* strain transformed with pBM-3 PnH®; lane 3 is vector pBM-3 PnH®, which serves as a positive control; lane 4 corresponds to the untransformed *Acidithiobacillus ferrooxidans* strain; lanes 2 and 5 are the negative controls with water; and lanes 6 and 7 correspond to the 100 pb and λ HindIII molecular standards, respectively. It is observed that the transformed strain (1) reveals the same band as the positive control (3), and that no band is observed in the negative control of the untransformed strain (4). So, the resulting recovered plasmid corresponds to pBM-3 PnH®.

The Plasmidial DNA isolated from the transformed strains of *Acidithiobacillus ferrooxidans* was used to transform a culture of *E. coli*. The result is shown in FIG. 6. B, where a culture plate containing Kanamycin, on which transformed *E. coli* strains grow, is shown.

The above examples must be held as illustrative of the invention, and in no case do they limit its scope which is described in the attached claims.

What is claimed is:

1. A plasmid for the transformation of bacteria of the *Acidithiobacillus* genus, comprising
    a replication origin isolated from a bacteria of the *Acidithiobacillus* genus, wherein the replication origin comprises the nucleic acid sequence of SEQ ID NO:1, SEQ ID NO:2, or the reverse complement thereof; and
    a nitrogenase promoter comprising the nucleic acid sequence of SEQ ID NO:3.

2. A plasmid according to claim 1, wherein the replication origin comprises the nucleic acid sequence of SEQ ID NO:1 or the reverse complement thereof.

3. A plasmid according to claim 1, wherein the replication origin comprises the nucleic acid sequence of SEQ ID NO:2 or the reverse complement thereof 4. A shuttle vector comprising the plasmid according to claim 1 together with a second replication origin that is specific for bacteria other than the *Acidithiobacillus* genus.

5. A shuttle vector according to claim 4, further comprising a multiple cloning site and at least one marker gene or reporter gene.

6. A shuttle vector according to claim 5, wherein the nitrogenase promoter is adjacent to the multiple-cloning site, and regulates the expression of a gene cloned into the shuttle vector at the multiple cloning site.

7. A shuttle vector according to claim 5, further comprising a nucleotide sequence adjacent to the multiple cloning site that encodes a 6-histidine peptide.

8. A shuttle vector according to claim 5, wherein the second replication origin is on pUC, ori ColE1, ori p15A, ori NTP1, ori pBR345, ori pBR322, or ori R6K.

9. A shuttle vector according to claim 5, wherein the reporter gene is lacZ (β-galactosidase), gfp (fluorescent green protein), or luc (luciferase).

10. A shuttle vector according to claim 9, wherein the reporter gene is lacZ.

11. A shuttle vector according to claim 5, wherein the marker gene is selected from genes that encode antibiotic resistance.

12. A shuttle vector according to claim 11, wherein the marker gene comprises a gene that encodes resistance to Kanamycin (kan).

13. A shuttle vector according to claim 8, wherein the second replication origin is ori pUC.

* * * * *

```
                        SEQUENCE LISTING

<160> NUMBER OF SEQ ID NOS: 3

<210> SEQ ID NO 1
<211> LENGTH: 1647
<212> TYPE: DNA
<213> ORGANISM: Acidithiobacillus ferrooxidans

<400> SEQUENCE: 1
attttcacta acatagcgac aacactaggt gcaatcaaat agttgccgtt tagtctgctt      60
taggttaaaa ggcaataacg ggaggcgctg tattggtgcc gcccgttatt tatggctgtt     120
atcagacatt acgatgaggt cgctcatttt gcttcctgtc aggatagttc aagacggcgc     180
tcaatgcgct ggatgcgctc atccaagctg tcataacgca catgctgctc tgcaatggag     240
cctgacaggt gtgccagata ttgcatgatc gttgacgttg tagcttccag gtcgtgatt      300 cggcttttaa tctctttgag atcgcgctca atacgatcct gcccagcctg aaagcgtttc     360
aggtgttcca gcatgaggtt ctctatctcg tttgccatag ttgtcttaga cggccttgcc     420
gcctgcctcc tgatgttggc cgcccttcac cacactaaac cctttcgcct tggccttatc     480
agctgttctc actgccttct ggtgagtagc ccctttccc ttccatccga attctggatt      540
caaggtgtaa gtgcggtttt ggcccattt tggtccaaca ataagcgcat ctaaactgat      600
gaggcgctta attgccctgt tgactcgcgc tcgatcgatg ttcatctccc gcgccatgtc     660
cgcctgagaa acggcgatat ggttctgata gtccagcttg cggagcaagt tcatcaagac     720
gcggaagccg tccacaccca aatcctgagc atgatcctcg aaaatcttga gtggtccttg     780
tgccatcgta aaaaacctcc ccttctcaaa agctactgga acgggccgct gaaccagcat     840
aggcactcgc tcggaaagta tctcaccagt atccctatca acgaagtcaa atgccatttt     900
ttgccccctt gttgactcca cagtcatcat tgatgattgt acagtcaaca aggggttttg     960
caagccatta ttttaacggc tgttttttg cccccttttt cttattctaa caggccgtgc     1020
cagcgaagcg ccgcacggac ccggtaagcc cccgcgatag cggtcgtcaa acccggccca    1080
ggagccgcta ggagtgggcg cttgcctcga cctatggtcg agccgccac gaaccctaa      1140 agggcctcac agggcattct agggcacctg tagcaagcat tccgccccac tggggcggtt    1200
gcggtagcgt cggtcgattt gcaagcaaat cgaccgccac tcctcgcccg actttgaccc    1260
ttcgggtcct gagctaaagc tattttttgtg acttgcaaca aaacaccacg attgtcgaaa   1320
gtttgggggg ggccgccaga gcgggggcaa tagcccggga gggggtcgat ccggcgaagg    1380
agcgcagcga ctgaggacag ggggaacggc acgttccccg ccggggatgt tcgtgggcgg    1440
tccgacgcag tcggagcaag cgcccactcc tttcttgcc agcaggacga ttaggtggca    1500
gtctaaccac tgtaaagcta gcctacccgt cgaacacgag cacccctga cggggttgcc     1560 catattcgac ggagactagc aagggggcgtt gccccttga ccccctgaca ctgccggagc    1620
gctttaacgt gacaagccac aaagaca                                        1647

<210> SEQ ID NO 2
<211> LENGTH: 1101
<212> TYPE: DNA
<213> ORGANISM: Acidithiobacillus thiooxidans

<400> SEQUENCE: 2
```

```
ttcgttacgg taacaaggcg aacggctcaa gccctctccc ccagacccccc tcacccagcc    60 cgtgcaggcc atacgatgca cgctgtagcc actattccgc cctctgggcg gttgcggatt   120
cgttcgacga tttgcaagca aatcaccgcc ctcaccgcg ctccctcctg ttttcctacg    180
agctaacgct tttcttttc ccgatagga atccagtgcc caccaccaaa agccccgcct     240
cgcggctatt atctgatata ggccgttcat tgcaccattg gcgagctcat tcattgcgca   300
ctttacaaaa attgcgcaat tttattgctt ttgagcaaac cagtacttta ccgttctgag   360
agacacgcca agggcatccg cgatagcctg ctgcgtatgc ccttgcgccc gcatcagcct   420
tgccgtagcc atgtcctgct cgctggacaa cttgcgggcc tgtccactgg ctatccctgc   480
ctcaacctga ttggaggctt tcctgccccg ctccgcctgc tgttctggcg tatgcgtccg   540
ctcgatgagg tcttgcaggc ctgcggggt catgttccgc caagtccacc cgctgatgct    600
cttagccgtg gccttcactt cggcaaaggg taagggctgc ggaaactcgc cgttaatggc   660
ctgtaatcgc tccaggacgg cttttgacca tcgaccaagc ccattgggtg cccaatactc   720
cctgacagcc ccgtaggccc agaaacgacc tgtatcgaac atggtgcagt tacgacccag   780
cccgaagctc tccgatgcgt cagagggcaa tctaggggtc ccctcagaat tcggaatata   840
aaacccggta aggaatttgg ttcatgccga atggcactat cgcaaacggt cgttttgag    900 gctccatcct gagaatgcac ggaaacgctg tgtttgctgg tgattgcgac gctcaaaaac   960
ggctctcaat ttcagttggc caggattatg ggttttgaga acagcagagt gggaatcttg  1020
accgaaagtc catgaacaag acatgctaga gatctccagg ccatcagatg tagcaaaatc  1080
atggggtcca acatccttaa c                                             1101

<210> SEQ ID NO 3
<211> LENGTH: 106
<212> TYPE: DNA
<213> ORGANISM: Acidithiobacillus ferrooxidans

<400> SEQUENCE: 3
ttttgcgcaa atttaaacga cctgcctgtc ttgccaatcc atcccgccca cttccttgac    60
aataccaacc ggtcggtctt agatgggggc cacactgaaa atttga                  106
```